United States Patent
Erickson et al.

(10) Patent No.: US 6,403,616 B1
(45) Date of Patent: Jun. 11, 2002

(54) CHEMICAL PROCESS AND PHARMACEUTICAL FORMULATION

(75) Inventors: Magnus Erickson, Västra Frölunda; Anders Gustavsson, Nykvarn; Lars Josefsson, Sävedalen, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/485,897

(22) PCT Filed: Nov. 15, 1999

(86) PCT No.: PCT/SE99/02093

§ 371 (c)(1),
(2), (4) Date: Feb. 17, 2000

(87) PCT Pub. No.: WO00/28975

PCT Pub. Date: May 25, 2000

(30) Foreign Application Priority Data

Nov. 18, 1998 (SE) .............................................. 9803952
Nov. 18, 1998 (SE) .............................................. 9803953

(51) Int. Cl.[7] ...................... A61K 31/44; C07D 401/12; C07D 235/28; C07D 471/04
(52) U.S. Cl. ........................ 514/338; 514/303; 514/393; 514/395; 546/118; 546/273.7; 548/303.7; 548/306.4
(58) Field of Search .............................. 546/273.7, 118; 548/306.4, 303.7; 515/303, 338, 395, 393

(56) References Cited

FOREIGN PATENT DOCUMENTS

| EP | 0519144 | 12/1992 |
|----|---------|---------|
| WO | 8602646 | 5/1986 |
| WO | 9427988 | 12/1994 |
| WO | 9501783 | 1/1995 |
| WO | 9501977 | 1/1995 |
| WO | 9532959 | 12/1995 |
| WO | 9601624 | 1/1996 |
| WO | 9601625 | 1/1996 |
| WO | 9702020 | 1/1997 |
| WO | 9741114 | 11/1997 |

OTHER PUBLICATIONS

Pilbrant and Cederberg, Development of an oral formulation of omeprazole, Scand. J. Gastroenterology, 1985; 20 (suppl. 108) pp. 113–120, Molndal, Sweden.

*Primary Examiner*—Bernard Dentz
(74) *Attorney, Agent, or Firm*—White & Case LLP

(57) ABSTRACT

Process for the manufacturing of slightly soluble or less soluble alkaline salts of substituted sulphinyl heterocycles containing an imidazole moiety with formula I

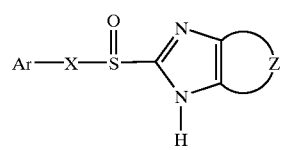

preferably alkaline salts of a proton pump inhibitor compound, wherein the process comprises the step of reacting the substituted sulphinyl heterocycle of Formula I with a source of the cation in the presence of a base, characterized by a washing step in which the prepared alkaline salt of the substituted sulphinyl compound is washed with a basic aqueous solvent mixture. The obtained bulk drug substance resulting in a bulk product that in an aqueous suspension of the substituted sulphinyl heterocycle having a pH not significantly lower than that of a saturated water solution of the pure compound prepared. Alternatively, the process for manufacturing a pharmaceutical dosage form comprising the active substance could be adjusted. For instance the pH of an aqueous suspension of the active substance is adjusted to a pH not significantly lower than that of a saturated water solution of the pure compound. The processes are preferably useful in the manufacturing of omeprazole magnesium salt or magnesium salt of one of its single enantiomers used in pharmaceutical dosage forms.

18 Claims, 1 Drawing Sheet

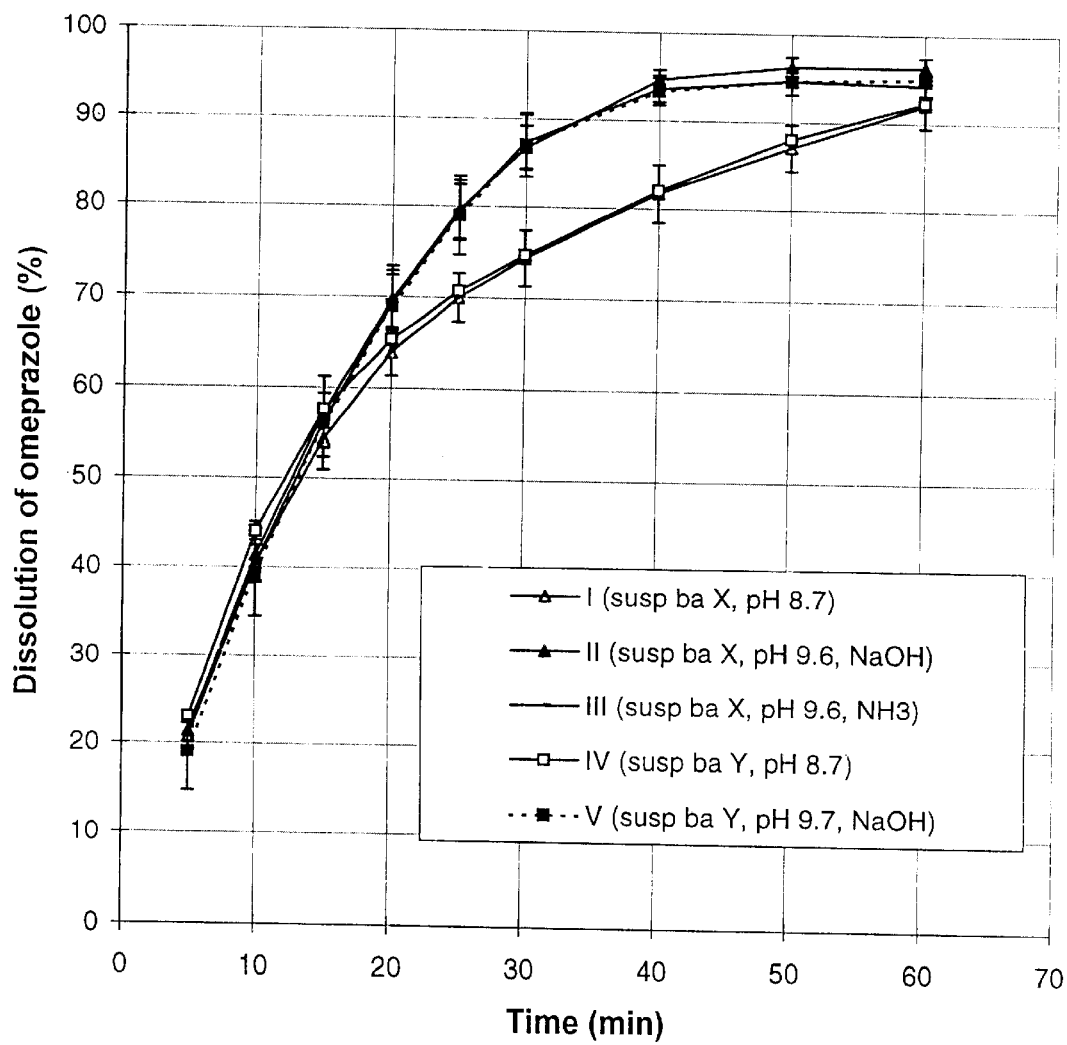

CHEMICAL PROCESS AND PHARMACEUTICAL FORMULATION

This application is a 371 of PCT/SE99/02093 filed Nov. 15, 1999.

FIELD OF THE INVENTION

The present invention relates to an improved process for the manufacturing of an alkaline salt of an acid susceptible proton pump inhibitor compound, such as a substituted sulphinyl heterocyclic compound containing an imidazole moiety. More specifically the invention is related to an improved process for the manufacturing of an alkaline salt of omeprazole or an alkaline salt of (S)-omeprazole, preferably magnesium salts of these compounds. The invention is also related to an improvement in the preparation of the pharmaceutical formulation and to products containing as the active ingredient a compound prepared by the claimed processes as well as the use of the products in medicine.

BACKGROUND OF THE INVENTION AND PRIOR ART

Substituted benzimidazoles such as for instance the compounds with the generic names omeprazole, lansoprazole, pantoprazole, rabeprazole and leminoprazole have properties making the compounds useful as inhibitors of gastric acid secretion. This class of compounds is known as proton pump inhibitors or $H^+,K^+$-ATPase inhibitors. There are a large number of patents and patent applications disclosing such proton pump inhibitors and processes for their manufacturing.

There is a general need in industry that pharmaceutically active compounds should be produced by processes giving products with properties, such as being easy to handle in full scale manufacturing and having good stability during storage, making them suitable for pharmaceutical preparations. The active substance, the drug, should also be presented in a form with such physico-chemical properties that are suitable for pharmaceutical manufacturing processing, and the drug should be released from the dosage form with a rate suitable for its intended pharmacological effect. Usually, it is the concern of the formulator to develop dosage forms with the desired properties. However, to obtain a good formulation, it is beneficial and important that the active substance as such is prepared and presented in the most suitable form.

WO 95/01977 discloses a magnesium salt of omeprazole with a specific degree of crystallinity making the claimed product especially suitable for pharmaceutical formulations; this is also discussed in WO 95/01783.

An efficient process for the manufacture of a magnesium salt of omeprazole is described in WO 97/41114. This process comprises mixing and reacting omeprazole with a weak base and a magnesium source and optionally the reaction takes place in the presence of an organic solvent. After the reaction is completed, the product is preferably crystallised from the filtrate.

Other processes related to the manufacture of alkaline salts of proton pump inhibitors are for instance disclosed in WO 94/27988, in which the preparation of the single enantiomers of omeprazole and alkaline salts thereof is described.

The present invention provides improvements over the prior art processes. It represents especially an improvement of the process described in WO 97/41114.

A pharmaceutical dosage form suitable for proton pump inhibitor compounds is for instance described in WO 96/01624. Said patent application describes preparation of small enteric coating layered pellets comprising the active substance. These enteric coating layered pellets are compressed into tablets. Preferably, the preparation of pellets containing the active substance is performed by spray layering the active substance onto seeds, such as for instance sugar spheres, and thereafter applying the enteric coating layer, optionally after a separating layer has first been applied to separate the active substance from the finally applied enteric coating layer.

Proton pump inhibitor compounds are acid susceptible and with respect to the stability properties of these compounds, it is obvious that an oral solid dosage form must be protected from contact with the acidic gastric juice and that active drug must be transferred in intact form to that part of the gastrointestinal tract where pH is near neutral and where rapid absorption can occur.

The rate of release of the drug from a pharmaceutical dosage form can influence the total extent of absorption of such a drug into the general circulation. Omeprazole and related drugs as well as dosage forms comprising these drugs have been investigated (See for instance Pilbrant and Cederberg, Scand. J. Gastroenterology 1985; 20 (suppl. 108) p. 113–120). The marketing approval for these products specifies limits for the rate of release of the drug from the pharmaceutical dosage form.

SUMMARY OF THE INVENTION

The present invention provides an improved process for the preparation of an alkaline salt of a substituted sulphinyl heterocycle containing an imidazole moiety and especially magnesium salts of substituted benzimidazole derivatives. The process results in a bulk product, which on addition of water, gives a suspension with a pH above a specified pH range. Said product is suitable for further processing into a pharmaceutical preparation. The release properties of such a pharmaceutical formulation comprising the new form of the active substance are improved. The claimed process provides especially a more suitable bulk drug product for pharmaceutical dosage forms, for intance a multiple unit tablet.

According to the improved process, an alkaline salt of a substituted sulphinyl heterocycle containing an imidazole moiety is prepared, and the process comprises a final step wherein a base is added to a washing solvent to adjust the pH of the solution, which solution is used in the final wash of the product. Preferably, a magnesium salt of the substituted sulphinyl heterocycle compound is prepared according to WO 97/41114, hereby included by reference, by mixing and reacting the substituted sulfinyl heterocycle compound with a weak base, preferably an amine or ammonia, and a magnesium source, such as an organic or inorganic magnesium salt or a combination of such salts. Thereafter the crystallised and isolated magnesium salt product is washed with a basic aqueous solvent mixture.

The process may also be used to prepare other salts of substituted sulphinyl heterocycles containing an imidazole moiety, for instance slightly soluble or less soluble salts, preferably a multivalent salt such as a calcium salt, by the use of a calcium source or any other suitable source of that cation. Slightly soluble or less soluble salts are defined in compliance with the European Pharmacopiea (Edition 3) under the heading "General notice".

The present invention also provides an improved process for the preparation of a pharmaceutical dosage form by spray layering of the active substance onto seeds, such as for instance sugar spheres. The active substance is preferably an acid susceptible drug selected from an alkaline salt of a substituted sulphinyl heterocycle containing an imidazole moiety. The active substance is suspended in an aqueous solution of a macromolecular binding agent. The obtained suspension should have a pH not significantly lower than that of a saturated water solution of the pure drug substance.

In one preferred embodiment, the claimed process relates to a process for the manufacturing of dosage forms comprising magnesium salts of substituted benzimidazole derivatives. More specifically, the process is related to the preparation of spray layered spheres with omeprazole magnesium in a water solution of a binding agent. The prepared pellets are covered by a separating layer and an enteric coating layer and filled into a capsule, or mixed with tablet excipients and compressed into a tableted multiple unit dosage form. Preferably, a tablet comprising a multiple of enteric coating layered units of omeprazole magnesium is prepared.

BRIEF DESCRIPTION OF THE DRAWINGS

FIG. 1 shows the result from testing the rate of release of omeprazole from sugar spheres spray layered with a suspension of omeprazole magnesium as prepared according to Example 2. Three graphs refer to pellets prepared according to the present invention and two graphs refer to reference pellets.

DETAILED DESCRIPTION OF THE INVENTION

According to one aspect, the present invention provides a novel method of preparing a slightly soluble or less soluble alkaline salt of a substituted sulphinyl heterocycle containing an imidazole moiety with the following formula I

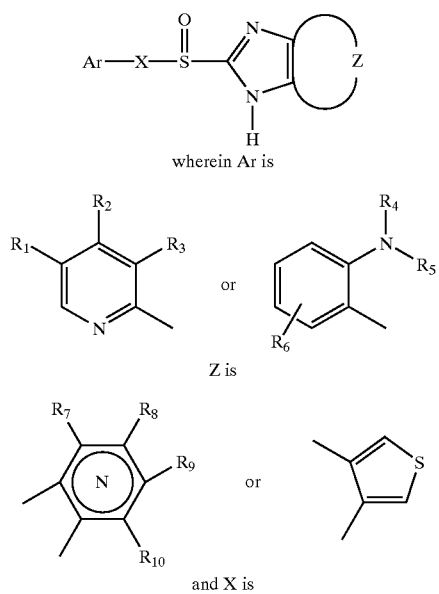

wherein Ar is

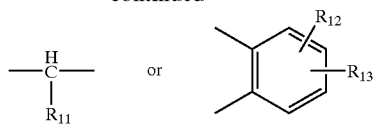

wherein
N inside the benzene ring of the benzimidazole moiety means that one of the carbon atoms substituted by $R_7$–$R_{10}$ optionally may be exchanged for a nitrogen atom without any substituents;

$R_1$, $R_2$ and $R_3$ are the same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

$R_4$ and $R_5$ are the same or different and selected from hydrogen, alkyl and aralkyl;

$R_6$ is hydrogen, halogen, trifluoromethyl, alkyl and alkoxy;

$R_7$–$R_{10}$ are the same or different and selected from hydrogen, alkyl, alkoxy, halogen, haloalkoxy, alkylcarbonyl, alkoxycarbonyl, oxazolyl, trifluoroalkyl, or adjacent groups $R_7$–$R_{10}$ form ring structures which may be further substituted;

$R_{11}$ is hydrogen or forms an alkylene chain together with $R_3$ and $R_{12}$ and $R_{13}$ are the same or different and selected from hydrogen, halogen or alkyl, and wherein alkyl groups, alkoxy groups and moieties thereof may be branched and straight $C_1$–$C_9$-chains or comprise cyclic alkyl groups, for example cycloalkylalkyl, which process comprises the step of reacting the substituted sulphinyl heterocycle of Formula I with a source of the cation in the presence of a base. The process is characterised by a washing step in which the prepared alkaline salt of the substituted sulphinyl compound is washed with a basic aqueous solvent mixture. Such a preferred basic aqueous solvent mixture comprises for instance sodium hydroxide or ammonia, and preferably a solvent mixture comprising an alcohol, sodium hydroxide and water is used. The obtained bulk drug substance will, in an aqueous suspension of the substituted sulphinyl heterocycle of Formula I, have a pH equal to or above that of a saturated water solution of the pure alkaline salt of the substituted sulphinyl compound prepared.

In general, the present invention is applicable for the manufacturing of a slightly soluble or a less soluble alkaline salt of a substituted sulphinyl heterocycle containing an imidazole moiety. The invention is exemplified with the manufacturing of omeprazole magnesium salt.

Preferably, the magnesium salt of omeprazole is prepared by reacting omeprazole with a magnesium source in the presence of a weak base as described in WO97/41114, and the crystallised and isolated magnesium salt of omeprazole is washed with a basic aqueous solvent mixture.

One purpose of the present invention is to secure a pH not significantly lower than that of a saturated water solution of the pure compound when the manufactured bulk drug substance is suspended in water. Preferably, a suspension of omeprazole magnesium should have a pH of 9.5 or above in a 10% (w/w) suspension of the bulk substance. To obtain a suitable pH (as measured in a 10% suspension), a small amount of a base is added to increase the pH of the wash solution in order keep the pH of the bulk drug substance, in water, at a value not significantly lower than that of a saturated water solution of the pure compound. As an example, pKa for omeprazole magnesium is 8.8, and theoretically the pH of a saturated solution of omeprazole magnesium in water is about 9.6 at room temperature.

A suitable non-volatile base to be added to the wash solution is sodium hydroxide which is added in an amount of not exceeding 0.1% (w/w) of the solid omeprazole magnesium and preferably not more than approximately 0.02%. Ammonia is another suitable base for the claimed process.

According to a second aspect, the invention provides an improved method of preparing a pharmaceutical dosage form comprising the step of spray layering the active substance suspended in an aqueous solution of a binding agent onto seeds, preferably sugar spheres. A suspension of the active substance in water, preferably 10–50 % (w/w), is mixed with a binding agent, and optionally wet-milled. The pH of the suspension is controlled and adjusted before spray layering onto sugar spheres in a fluid bed. In the following example, a 25% suspension of omeprazole magnesium is prepared. The pH of the suspension is controlled and/or adjusted to a value not significantly lower than that of a saturated water solution of pure omeprazole magnesium by addition of a base. Suitable bases are for instance sodium hydroxide and ammonia, which are added in an amount needed to raise the pH to a desirable value.

A saturated water solution of omeprazole magnesium has, theoretically, a pH of 9.6, and the aqueous suspension of omeprazole magnesium and binding agent should have a pH of 9.4 or above, and more preferably a pH of 9.5 or above.

One of the purposes of the present invention is to secure a pH not significantly lower than that of a saturated water solution of the pure compound when making the suspension for spray layering, i.e. when substance is suspended in an aqueous solution of the binding agent.

A suitable binding agent for the suspension of the active drug is a macromolecular agent, such as for instance celluloses such as hydroxypropyl methylcellulose, methylcellulose, hydroxypropyl cellulose and carboxymethylcellulose sodium, polyvinyl pyrrolidone, gelatine, sugars, starches and other pharmaceutically acceptable substances with cohesive properties. These binding agents can be used alone or in mixtures.

Furthermore, the suspension may comprise an alkaline reacting substance, in admixture with one or more pharmaceutically acceptable excipients. In addition to the binding agent, such excipients are for instance a disintegrating agent and/or a surface active ingredient.

The prepared spray layered units are enteric coated. Optionally the units are covered by a separating layer—before the enteric coating layer is applied—to separate the enteric coating layer from the active drug layer.

Suitable material and techniques for the seeds, enteric coating layering and the optional separating layer are known in the art. Preferred materials and techniques are for instance described in WO 96/01624, which is hereby included by reference.

Use of the Invention

Proton pump inhibitors are generally known to be useful for inhibiting gastric acid secretion in mammals and man by controlling gastric acid secretion at the final step of the acid secretory pathway. Thus, in a more general sense, it may be used for prevention and treatment of gastric-acid related diseases in mammals and man, including e.g. reflux oesophagitis, gastritis, duodenitis, gastric ulcers and duodenal ulcers. Furthermore, it may be used for treatment of other gastrointestinal disorders where gastric acid inhibitory effect is desirable e.g. in patients on non steroidal antiinflammatory drug (NSAID) therapy, in patients with non ulcer dyspepsia, in patients with symptomatic gastric-oesophageal reflux disease, and in patients with gastrinomas. It may also be used in patients in intensive care situations, in patients with acute upper gastrointestinal bleeding, pre-and postoperatively to prevent aspiration of gastric acid and to prevent and treat stress ulceration. Further, it may be useful in the treatment of psoriasis as well as in the treatment of Helicobacter infections and diseases related to these, as well as in the treatment or prophylaxis of inflammatory conditions in mammals, including man.

Prepared dosage forms comprising a drug substance prepared according to the invention are suitable for oral administration. The dose will depend on the nature and severity of the disease to be treated. The dose may also vary according to the age, body weight, and response of the individual patient. Children and patients with liver diseases as well as patients under long term treatment will generally benefit from doses that are somewhat lower than the average. In the treatment of other conditions higher doses than average will be used.

Preferably, a dose of the proton pump inhibitor, for instance 1–500 mg is administered once a day. Suitable doses comprise for instance about 5–100 mg of the substance, and more preferably 5–80 mg. The dosage form may be administered together with other suitable drugs, such as antibacterial compound(s), NSAID(s), motility stimulating agents, and/or antacids. The dosage form may alternatively be in the form of a tableted effervescent multiple unit dosage form.

The invention is further described and discussed in the following by examples. The intention of the examples is not to limiting the scope of the invention which scope is defined by the enclosed claims.

Results and Discussion

It is beneficial for the pharmaceutical processing that the bulk drug substance suspended in water will produce a pH in the suspension which is not significantly lower than that of a saturated water solution of the pure compound. For instance, a suspension of omeprazole magnesium should have a pH of about 9.6.

The invention is illustrated by Example 1 and Reference Example A describing dissolution rate from pharmaceutical dosage forms comprising sugar spheres that are spray layered with an aqueous suspension of omeprazole magnesium. As the results show, a pH significantly lower than that of a saturated water solution of pure omeprazole magnesium in the washing step of the manufacturing process of the bulk drug substance may cause a low dissolution rate of omeprazole magnesium from the prepared pellets (Reference example A). These results can be compared with a formulation comprising pellets prepared from omeprazole magnesium with a pH not significantly lower than that of a saturated water solution of pure omeprazole magnesium in the washing step of the manufacturing process of the bulk drug substance (Example 1). The mechanism behind this lowering of the dissolution rate from the pharmaceutical dosage form, might depend on co-precipitation of small amounts of the non-ionized and less soluble forms of the substance (in this case non-salt forms of omeprazole ) at the surface of the dried material. Such possible precipitation of omeprazole, non-salt form, will not disturb the dissolution rate from the pharmaceutical dosage form, if the pH in the aqueous suspension prepared from omeprazole magnesium and used for spray layering onto seeds is not significantly lower than that of a saturated water solution of pure omeprazole magnesium.

Furthermore, the invention is illustrated by Example 2 and Reference Example B. The prepared pellets were tested in USP dissolution apparatus with respect to release rate of omeprazole in phosphate buffer solution, pH 6.8; ionic strength I=0.16; temp 37° C.; stirring rate 100 rpm. The release of omeprazole was followed by spectrophotometric determination (302 nm) and the results are presented in FIG. 1.

The graphs show that the release of omeprazole can be increased by adjusting the pH to a value not significantly lower than that of a saturated water solution of the pure compound.

EXAMPLE 1

Examples of dissolution rate from pharmaceutical dosage forms manufactured from different batches of omeprazole magnesium prepared in accordance with the present invention.

Preparation

Multiple unit tablets comprising enteric coating layered pellets of omeprazole magnesium were prepared in accordance with the description in WO 96/01623, see Example 2. Omeprazole magnesium was prepared in accordance with WO 97/41114, and the omeprazole magnesium was washed with a basic aqueous solvent mixture (methanol/water) containing a small amount of sodium hydroxide corresponding to 0.02% w/w of the omeprazole magnesium substance. The prepared omeprazole magnesium was used in the manufacturing of multiple unit tablets.

Analysis

The pH-value of a water suspension (10% w/w) of omeprazole magnesium was measured (table I, column II), and the dissolution from manufactured tableted dosage forms of the respective batch of omeprazole magnesium was determined (table I, column III). The amount of omeprazole released within 30 minutes in a buffer solution was determined. The tablets were pre-exposed to 0.1 M hydrochloric acid at 37° C. for 2 hours.

TABLE I pH-value of the aqueous suspension of omeprazole-Mg, and dissolution of omeprazole from a multiple unit tablet prepared from such omeprazole-Mg

| Batch | pH of omeprazole -Mg (10% w/w in water) | Dissolution (%, 30 min; n = 6) |
|---|---|---|
| Susp. I* | 9.7 | 94 (101–93) |
| Susp. II* | 9.6 | 95 (93–97) |
| Susp. III** | 10.3 | 95 (92–99) |
| Susp. IV** | 10.1 | 93 (92–97) |

*pH >9.5 no addition of base needed in the wash solution.
**Base added to the wash solution

Reference Example A

Examples of dissolution rate from pharmaceutical dosage forms manufactured from two different batches of omeprazole magnesium prepared without any addition of a base to the solvent used for washing of the omeprazole magnesium.

Preparation and Analysis

In accordance with Example 1, tableted dosage form were prepared from batches of omeprazole magnesium having a pH-value of a 10% w/w suspension in water significantly lower than that of a saturated solution of the pure compound and the corresponding dissolution rate from manufactured tablets was measured.

TABLE A pH-value of the aqueous suspension of omeprazole-Mg, and dissolution of omeprazole from a multiple unit tablet prepared from such omeprazole-Mg

| Batch | pH of omeprazole -Mg (10% w/w in water) | Dissolution (%, 30 min; n = 6) |
|---|---|---|
| Susp. A I | 9.2 | 77 (81–73) |
| Susp. A II | 9.2 | 71 (69–73) |

The results from Example 1 and Reference Example A show that the addition of a base to the wash solution in the final washing step in the manufacturing of omeprazole magnesium, to increase the pH (resulting in an aqueous suspension of the omeprazole magnesium having a pH not significantly lower than that of a saturated water solution of pure omeprazole magnesium), has an influence on the dissolution rate from a tableted enteric coated pharmaceutical dosage form comprising said omeprazole magnesium.

EXAMPLE 2

Core material comprising omeprazole magnesium was prepared by spray layering a suspension of omeprazole magnesium onto sugar sphere seeds (0.25–0.35 mm) in a fluid bed apparatus.

Composition of the suspension:

| | |
|---|---|
| omeprazole magnesium | 25.0% (w/w) |
| hydroxypropyl methylcellulose | 3.75% (w/w) |
| water | 71.25% (w/w) |

The pH of the suspension was controlled and adjusted by addition of a suitable amount of sodium hydroxide or ammonia to pH 9.6–9.7. Thereafter, 400–600 g of suspension was sprayed onto 100–150 g sugar spheres (0.25–0.35 mm). Three prepared experimental pellets were tested as described below, and results are shown in FIG. 1.

Reference Example B

Core material comprising omeprazole magnesium was prepared by spray layering a suspension of omeprazole magnesium onto sugar sphere seeds (0.25–0.35 mm) in a fluid bed apparatus as described in Example 2. The suspension of omeprazole magnesium had a pH value of 8.7 in both experiments. The prepared pellets were tested as described below, and the results are shown in FIG. 1.

The prepared pellets were tested in USP Dissolution Apparatus No 2 (paddle) with respect to release rate of omeprazole in phosphate buffer solution pH 6.8; ionic strength 0.16; temperature 37° C.; stirring rate 100 rpm. The release of omeprazole was followed by spectrophotometric determination (302 nm).

What is claimed is:

1. A process for the manufacturing of slightly soluble or less soluble alkaline salts of substituted sulphinyl heterocycles containing an imidazole moiety with Formula I in the form of a racemate, one of the single enantiomers or an enantiomeric enriched form,

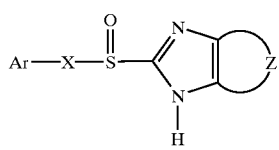

wherein
Ar is

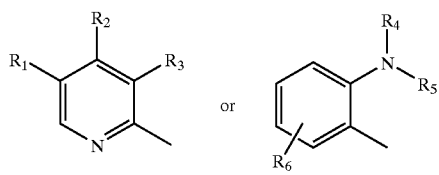

Z is

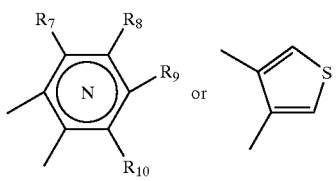

and X is

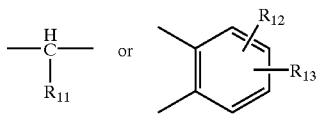

wherein
  N inside the benzene ring of the benzimidazole moiety means that one of the carbon atoms substituted by $R_7$–$R_{10}$ optionally may be exchanged for a nitrogen atom without any substituents;
  $R_1$, $R_2$ and $R_3$ are the same or different and selected from the group consisting of hydrogen, alkyl, alkylthio, alkoxy, alkoxy substituted by fluorine, alkoxyalkoxy, dialkylamino, piperidino, morpholino, halogen, phenylalkyl and phenylalkoxy;
  $R_4$ and $R_5$ are the same or different and selected from the group consisting of hydrogen, alkyl and aralkyl;
  $R_6$ is selected from the group consisting of hydrogen, halogen, trifluoromethyl, alkyl and alkoxy;
  $R_7$–$R_{10}$ are the same or different and selected from the group consisting of hydrogen, alkyl, alkoxy, halogen, haloalkoxy, alkylcarbonyl, alkoxycarbonyl, oxazolyl, and trifluoroalkyl, or adjacent groups $R_7$–$R_{10}$ form ring structures which may be further substituted;
  $R_{11}$ is hydrogen or forms an alkylene chain together with $R_3$ and
  $R_{12}$ and $R_{13}$ are the same or different and selected from the group consisting of hydrogen, halogen and alkyl, and wherein alkyl groups, alkoxy groups and moieties thereof may be branched and straight $C_1$–$C_9$-chains or comprise cyclic alkyl groups, which process comprises the step of reacting the substituted sulphinyl heterocycle of Formula I with a source of the cation in the presence of a base, and a washing step in which the prepared alkaline salt of the substituted sulphinyl compound is washed with a basic aqueous solvent mixture.

2. The process according to claim 1, wherein the slightly soluble or less soluble alkaline salt of Formula I is a magnesium salt of the substituted sulphinyl heterocycle containing an imidazole moiety with Formula I.

3. The process according to claim 1, wherein the pH of the basic aqueous solvent mixture is adjusted by addition of a base to a pH resulting in a bulk product, that in an aqueous suspension of the substituted sulphinyl heterocycle, having a pH of not more than 0.2 pH-units lower than that of a saturated water solution of the pure alkaline salt of the substituted sulphinyl compound.

4. The process according to claim 3, wherein the base is sodium hydroxide or ammonia.

5. The process according to claim 1, wherein a magnesium salt of omeprazole is prepared.

6. The process according to claim 5, wherein the base added to the wash solution is sodium hydroxide in an amount not exceeding 0.1% (w/w) of the solid omeprazole magnesium.

7. The process according to claim 5, wherein the base added to the wash solution is sodium hydroxide in an amount of not exceeding 0.02% (w/w) of the solid omeprazole magnesium.

8. The process according to claim 1, wherein a magnesium salt of the (S)-omeprazole is prepared.

9. A pharmaceutical dosage form comprising a drug substance prepared according to any of claims 1–8.

10. A method of treatment of gastrointestinal diseases comprising the administration to a patient in the need thereof of a pharmaceutical dosage form comprising a drug substance prepared according to any of claims 1–8.

11. A process for the manufacture of a pharmaceutical dosage form comprising as active substance a compound manufactured according to any of claims 1–8, the process comprising the step of spray layering the active substance in the form of a suspension of the substance in a water solution of a binding agent onto seeds, wherein the pH of the aqeuous suspension of the active substance is adjusted to a pH of not more than 0.2 pH-units lower than that of a saturated water solution of the pure alkaline salt of the substituted sulphinyl compound.

12. The process according to claim 11, wherein the suspension of the active substance is wet-milled to a micronised suspension.

13. The process according to claim 11, wherein the pH is adjusted by addition of a base.

14. the process according to claim 13, wherein the base is sodium hydroxide or ammonia.

15. The process according to claim 11, wherein the active substance is a magnesium salt of omeprazole.

16. The process according to claim 11, wherein the active substance is a magnesium salt of (S)-omeprazole.

17. A pharmaceutical dosage form prepared according to claim 11.

18. A method of treatment of gastrointestinal diseases comprising the administration to a patient in the need thereof of a pharmaceutical dosage according to claim 11.

* * * * *